United States Patent [19]

Kawanami et al.

[11] Patent Number: 5,341,672

[45] Date of Patent: Aug. 30, 1994

[54] METHOD FOR MEASUREMENT OF POLYMER MOLECULAR WEIGHT BASED UPON A TEMPERATURE DIFFERENCE

[75] Inventors: Norio Kawanami; Kiyotaka Kondo; Yoshihiro Ikeda; Tooru Nakagawa, both of Hyogo; Kensuke Itoh, Tokyo; Yukihiro Saiki, Saitama; Saburo Ishii; Kenji Aoyama, both of Tokyo, all of Japan

[73] Assignees: Kanegafuchi Chemical Industry Co., Ltd.; Snow Brand Milk Products Co., Ltd., both of Japan

[21] Appl. No.: 155,657

[22] Filed: Nov. 22, 1993

Related U.S. Application Data

[63] Continuation of Ser. No. 871,735, Apr. 21, 1992, abandoned.

[30] Foreign Application Priority Data

Apr. 22, 1991 [JP] Japan .................... 3-90454
Apr. 22, 1991 [JP] Japan .................... 3-90455

[51] Int. Cl.$^5$ ........................... G01N 25/00
[52] U.S. Cl. .......................... 73/64.54; 374/45
[58] Field of Search ............ 374/45; 73/64.54, 54.42, 73/54.01

[56] References Cited

U.S. PATENT DOCUMENTS

| | | | |
|---|---|---|---|
| 2,986,925 | 6/1961 | Gentry, Jr. et al. | 73/54.42 |
| 3,164,982 | 1/1965 | Pasternak et al. | 73/64.54 |
| 3,420,096 | 1/1969 | Hoyt | 73/64.54 |
| 3,753,369 | 8/1973 | Fowler et al. | 73/54.42 |
| 3,837,217 | 9/1974 | Schulz | 73/61.52 |
| 3,930,399 | 1/1976 | Munk | 73/54.42 |
| 4,578,988 | 4/1986 | Hori et al. | 374/43 |
| 4,762,427 | 8/1988 | Hori et al. | 374/45 |
| 4,775,943 | 10/1988 | Chamberlin et al. | 364/497 |
| 4,852,388 | 8/1989 | Park et al. | 73/54.15 |
| 4,947,678 | 8/1990 | Hori et al. | 73/54.42 |

FOREIGN PATENT DOCUMENTS

| | | | |
|---|---|---|---|
| 0632439 | 1/1928 | France | 73/54.42 |
| 60-152943 | 8/1985 | Japan | . |
| 62-56849 | 12/1987 | Japan | . |
| 2-153936 | 6/1990 | Japan | . |

OTHER PUBLICATIONS

Rosen, S., "Fundamental Principles of Polymeric Materials," published by John Wiley & Sons, Chapter 7 and 13.2 (1982).

Derwent Publications Ltd., London, Molecular Weight and Concentration Determn, 72–65440T, Week 7241 SU 325543 (no date) (only abstract considered).

Derwent Publications Ltd., London, 87–055807/08, Mar. 1987 SU 1242799 (Jul. 7, 1986) (only abstract considered).

Primary Examiner—Diego F. F. Gutierrez
Attorney, Agent, or Firm—Wegner, Cantor, Mueller & Player

[57] ABSTRACT

A molecular weight of a polymer is measured by a process including steps of: heating a polymer portion with a heating device, measuring, with a temperature measuring device, the difference between temperatures of at least two points of the polymer portion at each of which the polymer portion is subjected to a thermally different influence from each other by the heating device, and estimating the molecular weight of the polymer which corresponds to the difference between the temperatures obtained by the measuring step according to a relationship between the temperature difference and the molecular weight of the polymer which relationship has been beforehand obtained.

2 Claims, 3 Drawing Sheets

METHOD FOR MEASUREMENT OF POLYMER MOLECULAR WEIGHT BASED UPON A TEMPERATURE DIFFERENCE

This application is a continuation of U.S. application Ser. No. 07/871,735 filed Apr. 21, 1992, now abandoned.

BACKGROUND OF THE INVENTION

1. Field of the Invention

The present invention relates to a method and an apparatus for the measurement of a molecular weight of a polymer including an oligomer.

2. Description of the Related Art

When a molecular weight of a polymer is measured, a viscosity-average molecular weight ($M\eta$) is generally used. Measurement of the viscosity-average molecular weight comprises measuring the viscosity of a diluted solution of the polymer using a commercial Ubelohde-type capillary viscometer and then calculating the molecular weight from a viscosity value with a specific equation for the specific polymer which defines a relationship between the viscosity and the polymer molecular weight. This method of measurement is sometimes referred to as the "Ubelohde method".

In order to carry out such a molecular weight measurement in which the viscosity measurement is utilized, it is required to pretreat, for example, dilute and purify, a polymer sample, so that it takes about from one to two hours to obtain measurement results. In addition, strict temperature control during the measurement, such as 30°±0.25° C., is necessary. Also, less skill of the measurement gives data with a larger error. In a polymerization operation, such viscosity measurement is carried out after the pretreatment of the polymer which is sampled from a reactor, and then it should be determined whether a desired polymer molecular weight is reached on the basis of the result of the viscosity measurement. If the desired molecular weight has not been reached, the polymerization operation should be continued.

As described above, when the molecular weight measurement is carried out in which the viscosity measurement is utilized, time-consuming manual analyses are required and errors can occur due to the unskillfulness of the individual operator so that the polymerization period can vary depending on the individual operator.

SUMMARY OF THE INVENTION

It is an object of the present invention to provide a method for the accurate measurement of a molecular weight of a polymer in a short time period in order to efficiently carry out a polymerization operation.

The above object is achieved by a method for the measurement of molecular weight of a polymer which comprises the steps of:

heating a polymer portion with heating means, measuring, with temperature measuring means, a difference between temperatures of at least two points of the polymer portion at each of which the polymer portion is subjected to a thermally different influence from each other by the heating means, and estimating the molecular weight of the polymer which corresponds to the difference between the temperatures obtained by the measuring step according to a relationship between the temperature difference and the molecular weight of the polymer which relationship has been beforehand obtained.

The above object can be advantageously achieved if the heating means also operates as the temperature measuring means which measures the temperature at one point of the at least two points.

DETAILED DESCRIPTION OF THE INVENTION

Figure 1:
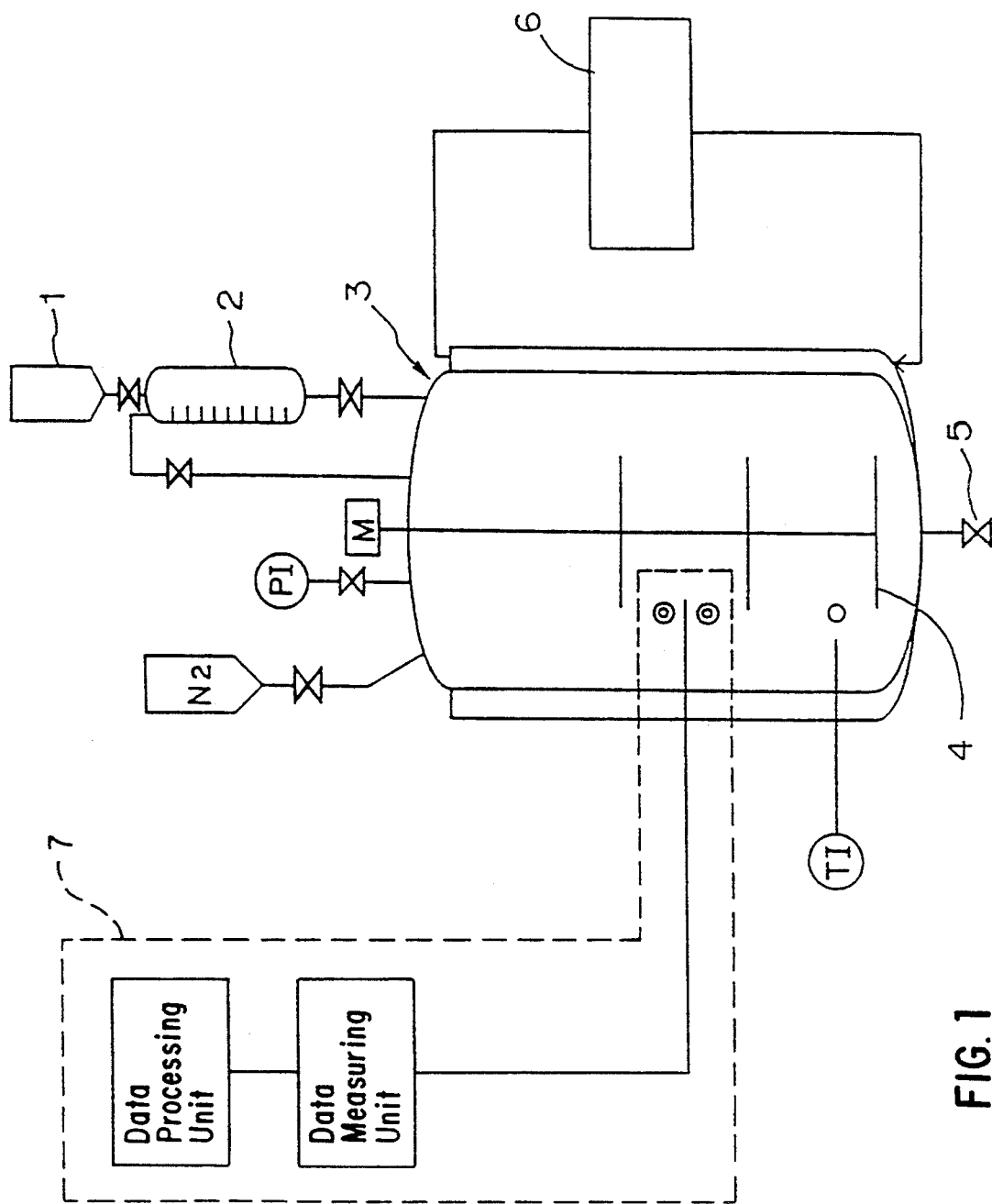
FIG. 1 schematically shows an example of a reactor vessel in which a polymerization operation is carried out by the method according to the present invention.

The present invention is on the basis of the following ideas. The reference number 1 denotes a starting material container, 2 denotes a starting material metering container, 3 denotes a stirred tank reactor, 4 denotes a stirrer, 5 denotes a discharge valve, 6 denotes a temperature controlling unit and 7 denotes a kinematic viscosity monitoring system.

Generally, dissipation of heat supplied to a material is greatly influenced by flow properties of the material, especially the viscosity of the material. That is, the heat transfer rate through a material having a higher viscosity is smaller than the heat transfer rate through a material having a lower viscosity. Thus, the viscosity of a polymer can be determined by measuring the heat transfer properties of the polymer, and then the molecular weight of the polymer can be estimated from the determined viscosity using a relationship between the viscosity and the molecular weight which has been beforehand obtained in a conventional manner.

It is known that the viscosity of a material other than a polymer maybe estimated from its heat transfer property. See, for example Japanese Patent Kokai Publication No. 152943/1985 (corresponding to U.S. Pat. No. 4,578,988).

However, it is not known to estimate the viscosity of a polymer from its heat transfer property and then to estimate the polymer's molecular weight from results obtained by the viscosity estimation.

The heat transfer property is, in fact, suitably measured as a temperature difference formed by balance of an amount of heat supplied to a system and an amount of heat dissipated from the system. The viscosity is merely a kind of a parameter mathematically lying between the heat transfer property (or the temperature difference) and the molecular weight of the polymer, and in practice, a direct relationship between the temperature difference and the polymer molecular weight can be obtained.

The method according to the present invention is very convenient and also provides an excellent effect that the polymer molecular weight is measured with substantially the same accuracy as that of the conventional viscosity method (Ubelohde method) as described in the above description of the related art. In addition, the strict temperature control (for example ±0.25° C.) during the measurement as required in the conventional viscosity method is not necessary in the present method but considerably rough control such as ±2°–3° C. is sufficient. The present method may be applied to polymer molecular weight measurement in which high accuracy is required.

The polymer of which molecular weight can be measured by the present method includes, but is not limited to, an olefin polymer (for example polyethylene), a vinyl polymer (for example polyvinyl chloride), a diene polymer (for example polybutadiene), a ring opening polymerization polymer (for example polypropylene glycol), a polycondensation-polyaddition polymer (for example oligoester acrylate), a petroleum resin polymer (for example $C_5$ petroleum resin), a fluorine-containing polymer (for example fluoroolefin telomer), a silicone polymer (for example cyclic dimetyl polysiloxane) and a polysulfide polymer. In particular, the present method is suitably used in the polymerization operation of a synthetic organic polymer, especially ring-opening polymerization of, for example, polyoxyalkylene. With respect to a range of the molecular weight of the polymer to be measured, the present method is particularly suitable for the molecular weight measurement of a polymer having a comparatively low molecular weight (such as an oligomer) of, for example, up to about $5 \times 10^4$, preferably up to about $3 \times 10^4$, and more preferably up to about $2 \times 10^4$.

In the case of a polymer of a too high molecular weight, even though the molecular weight measurement itself of a polymer portion around the temperature measuring points is carried out correctly, such a polymer portion may not be a representative of the entire polymer system in a reactor since the viscosity of the polymer is so high that complete mixing within the reactor is not necessarily possible, and thus the polymer phase may not be homogeneous. Therefore, in the present method, the viscosity of the polymer is preferably less than 1000 poise, more preferably less than 500 poise, and most preferably less than 100 poise.

In the present invention, the heating means may be any type of a suitable means which can uniformly supply an amount of heat to the polymer portion in which the temperatures are measured at least at two points. For example, a conventional sheathed heater made of stainless steel may be used. In a preferred embodiment, a sensor disclosed in Japanese Patent Kokai Publication No. 56849/1987 (corresponding to U.S. Pat. No. 4,762,427) may be used as the heating means of the present invention. In the present method, "heating a polymer portion with the heating means" is intended to mean supply of a certain fixed amount of heat to the polymer portion (in which the temperature difference is measured) in a certain period of time, namely, uniformly heating of the polymer portion. The heating may be temporary, intermittent or continuous.

In the present invention, the temperature measuring means may be any type of a suitable device which can measure the temperature at a point of the polymer portion. For example, a resistance thermometer can be used. Since the temperature difference should be measured as the heat transfer property in the present invention, temperatures of at least two points of the polymer portion must be measured which are thermally influenced differently from each other. When the two points of the polymer portion are thermally influenced similarly to each other, the temperatures at the two points are the same and no temperature difference exists in the polymer portion so that the heat transfer property as the temperature difference cannot be obtained. "At least two" means that at least one datum on the temperature difference has to be obtained. Temperatures at three or more points may be measured and two or more temperature differences may be obtained, and then for example an average temperature difference of the three differences may be used as the temperature difference of the present method. "Thermally influenced" means that the temperature of the polymer portion at the temperature measuring point is influenced by the heating with the heating means, when such a polymer portion is heated. If an amount of heat supplied to the polymer portion is too small, a point in a polymer portion far from the heating means may not be thermally influenced. Thus, the measurement at such a point does not provide an accurate molecular weight.

Taking account of some measurement error on the temperature measurement itself, it is preferred to measure the temperatures of the two points of the polymer portion both of which are located near the heating means and which are separated by a proper certain distance. Especially, it is preferred that one point of the two at which temperatures are to be measured is very close to the heating means. Thus, in the most preferred embodiment, a device may be used in which a heating means and a temperature measuring means are combined together. Such a device may be a thermometer in which a small amount of current is supplied to a resistance element confined in a stainless steel made tube to generate an amount of heat, and the temperature of the heat-generating resistance element itself can be measured. The at least two points at which the temperatures of the polymer portion are measured are so selected that the temperatures at the at least two points are different from each other, and, preferably, the difference between the two temperatures is large. The distance between the two points at which temperature of the polymer portion is to be measured depends on the material of which molecular weight is to be measured and also depends on whether a fluid of which molecular weight is to be measured is a static system or a dynamic system. Generally, in the case of the static system, the distance may be in the range of 20–50 mm, preferably 20–40 mm, more preferably 20–30 mm, and in the case of the dynamic system, the distance may be in the range of preferably 10–30, more preferably 10–20 mm, for example about 10 mm.

In the present method, no additional operation rather than the measurement of the temperature difference is required, and the polymer molecular weight is immediately estimated in a proper manner according to the relationship between the temperature difference and the polymer molecular weight which relation has been beforehand obtained.

Since the temperature of the polymer may be measured in real time, the present invention may be used not only in the static system but also in the dynamic system in the meaning of polymer molecular weight change and polymer fluidity. For example, the present invention may be used in the case in which the system is stirred or the system is static and/or in the case in which the polymer molecular weight is not changed or is changing.

In principle, in the present invention, the relationship between the polymer viscosity and the polymer molecular weight should be obtained beforehand. However, the relationship may depend on a temperature of the polymer system. When the relationship between the temperature difference and the polymer molecular weight is used, the molecular weight from the viscosity measurement may be obtained according to a previously obtained relationship between the polymer molecular weight and the polymer viscosity combined with a temperature of the polymer system as a parameter. Since, in the practice of the present method, the relationship between the temperature difference and the molecular weight is directly obtained as described above, it is required to grasp beforehand how the relationship depends on the system temperature (thus, the polymer temperature). Therefore, in a preferred embodiment, relationships between the temperature difference and the molecular weight are obtained before the polymerization operation at some different temperatures around which the polymerization operation is carried out in practice.

Since several different relationships may have been previously obtained for several different system temperatures, it may be a question which temperature should be selected as the practical system temperature since two different temperatures at two different points of the polymer portion are measured. However, the difference between the temperatures of the two points is not large enough to significantly influence the viscosity measurement beyond measurement tolerances. Thus, for example, an arithmetic average temperature of the temperatures at the two points or one of the two temperatures may be used as the system temperature.

The present method can be used in any case in which the polymer molecular weight is to be estimated, and it is particularly suitable in the case in which a subsequent operation is to be selected during the polymerization process according to the polymer molecular weight. In the case in which molecular weight data are required in real time, since the polymer molecular weight may be estimated on-line, the next operation can be selected without a time lag so that polymer productivity is improved.

With respect to the desired polymer system, the relationship between the polymer molecular weight and the temperature difference between the sensors at a desired system temperature has been previously obtained as a calibration curve, and in the practical polymerization operation, only the temperature difference is measured and then the polymer molecular weight is estimated according to the calibration curve. Optionally, in order to confirm the calibration curve, it may be advisable that a sample is obtained from the polymerization system during the polymerization process and the polymer molecular weight can be measured by the conventional method such as the Ubelohde method, and then estimated values of the molecular weight by the present method and by the conventional method are compared so that a state of the system under polymerization is the same as that when the calibration curve has been obtained. For example, there may be a case in which the estimated molecular weights by the two methods (the conventional method and the present method) are different, that is, the checked point by the conventional method deviates from the calibration curve because of, for example, difference in a lot number of a starting material and/or the presence of impurities in the starting material. However, even in such a case, the calibration curve which has been previously obtained can be used depending on the desired molecular weight. When more accurate control of the polymer molecular weight is required, the calibration curve may be moved in parallel along a direction of the temperature difference so that the checked point should be on the moved calibration curve to obtain a new calibration curve, if the same kind of polymerization is carried out as when the calibration curve was obtained. Then, the polymer molecular weight is estimated from the measured temperature difference by using the new calibration curve. It is found that there is no problem in the practical polymerization when a curve moved in parallel is used as the new calibration curve.

In particular, in the case where a starting polymer having a low molecular weight which has been known is polymerized to have a polymer having a larger molecular weight, or in the case where the molecular weight measurement is carried out more than once during the polymerization, extremely accurate measurement of the polymer molecular weight is possible when the calibration curve is moved in parallel while keeping its shape.

In addition, the present invention provides an apparatus for the polymer molecular weight measurement, which comprises:

heating means for heating the polypher portion, and temperature measuring means for measuring temperature difference between at least two points of the polymer portion at each point of which the polymer portion is subjected to a thermally different influence from each other by the heating means.

In the preferred embodiment, the apparatus according to the present invention further comprises a data processing unit which stores the relationship between the polymer molecular weight and the temperature difference, and which can estimate the polymer molecular weight immediately from the measured temperature difference using the relationship.

The present invention will be hereinafter explained concretely by Examples.

EXAMPLE 1

This Example will be explained with reference to the drawing of FIG. 1 showing a jacketed stirred tank reactor.

An alcoholate compound (20 kg) of polypropylene glycol (PPG) more than 90% of which terminal OH groups had been converted to alkoxide groups (—ONa) was charged in the stirred tank reactor 3 through the starting material container 1 and the starting material metering container 2. After the charge, a vapor phase in the reactor was replaced with $N_2$, and the content of the reactor was heated to a desired temperature (130° C.) with the temperature control unit 6. After the temperature elevation, the kinematic viscosity monitoring system 7 (commercially available from JEOL, Tokyo, Japan) was switched on to start measurement of the temperature difference between a heated point and a non-heated point (the temperature difference between the two points of the polymer portion of the polymerization system).

One sensor of the monitoring system was a thermometer comprising a resistance element which is confined in a stainless steel made tube and through which current of 400 mA is passed to generate an amount of heat, and can measure the temperature of the sensor itself. The other sensor was a usual resistance thermometer which was spaced from the one sensor by a distance of 10 mm.

Figure 2:
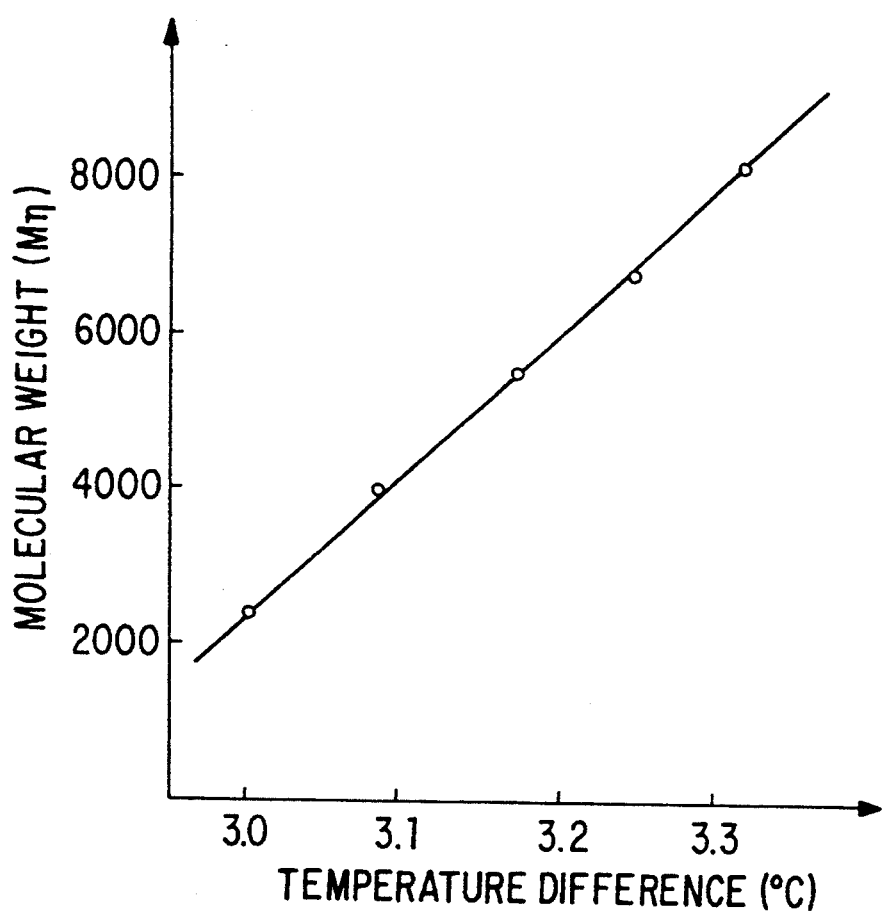
FIG. 2 shows a graph in which results obtained in Example 1 are plotted.

Then, a polyhalide compound as a molecular weight increasing agent was dropped from the metering container 2 and the temperature difference was successively measured by the kinematic viscosity monitoring system 7. Simultaneously, the polymer molecular weight was measured by an Ubelohde capillary viscometer ($M\eta$). By plotting the measured data of the temperature difference and the polymer molecular weight (Mη), a graph shown in FIG. 2 was obtained as a calibration curve.

It was found that when the same polymerization operation as described above was repeated and the polymer molecular weight was estimated using the calibration curve obtained as described above, the estimated molecular weight was the same as that obtained by using the Ubelohde viscometer (Mη) with an error of about ±1%. It is clearly understood that according to the present invention, the polymer molecular weight is estimated with the same accuracy as in the Ubelohde method.

The above polymerization of the alcoholate compound (starting molecular weight Mo=2400) was carried out by continuously dropping the molecular weight increasing agent while monitoring the polymer molecular weight by using the calibration curve obtained as described above. The polymer molecular weight was successively estimated with the calibration curve. After one hour a desired molecular weight (8100) was found to be reached and then the addition of the agent was stopped. The molecular weight of the end product was measured by the Ubelohde method and found to have the molecular weight of 8150.

COMPARATIVE EXAMPLE 1

The same polymerization operation as in Example 1 was carried out according to the molecular weight measurement by the Ubelohde method (the starting molecular weight was 2400, and the desired molecular weight was 8100).

When such a conventional method is used for the measurement of the polymer molecular weight, the molecular weight cannot be measured at a real time. Therefore, the molecular weight increasing agent cannot be dropped continuously. Since it is undesirable that the polymer molecular weight considerably exceeds the desired molecular weight, the a slightly less amount of the agent should be supplied than an amount which was required in order to attain the desired molecular weight (8100). After the molecular weight has approached near 8100, an additional small amount of the agent should be added to advance the polymerization ahead a little to create the polymer having the desired molecular weight.

The molecular weight increasing agent was initially added at a time in the reactor in an amount which is slightly less than an amount required to provide the desired polymer molecular weight with the Ubelohde method (Mη=8100). One hour after the addition, the polymer from the reactor was sampled. The molecular weight of the polymer sample was measured by the conventional method (Ubelohde method) and found to be Mη=7800. (It took about one and half hours to obtain the molecular weight.) This molecular weight was smaller by 300 than the desired molecular weight. Then, the additional agent was added at a time in an amount which corresponds to an amount required to increase the molecular weight by 300. After 30 minutes from the second addition of the agent, the polymer molecular weight was measured and found to be Mη=8150 (it also took about one and half hours to obtain the molecular weight), and then the polymerization process was stopped.

As seen from the above, it took a very long time to produce the polymer having the desired molecular weight since it was necessary to decide whether the polymerization should be continued on the basis of the molecular weight obtained by the conventional method. In fact, it took about four and half hours from the start of the polymerization to produce the desired polymer.

EXAMPLE 2

The alcoholate compound of polypropylene glycol (PPG) more than 90% of which terminal OH groups had been converted to alkoxide groups and which had been produced under different conditions from those in the case of the alcoholate of Example 1 was polymerized in the same conditions as in Example 1. As in Example 1, the relationship between the temperature difference and the molecular weight by Ubelohde method was obtained.

Figure 3:
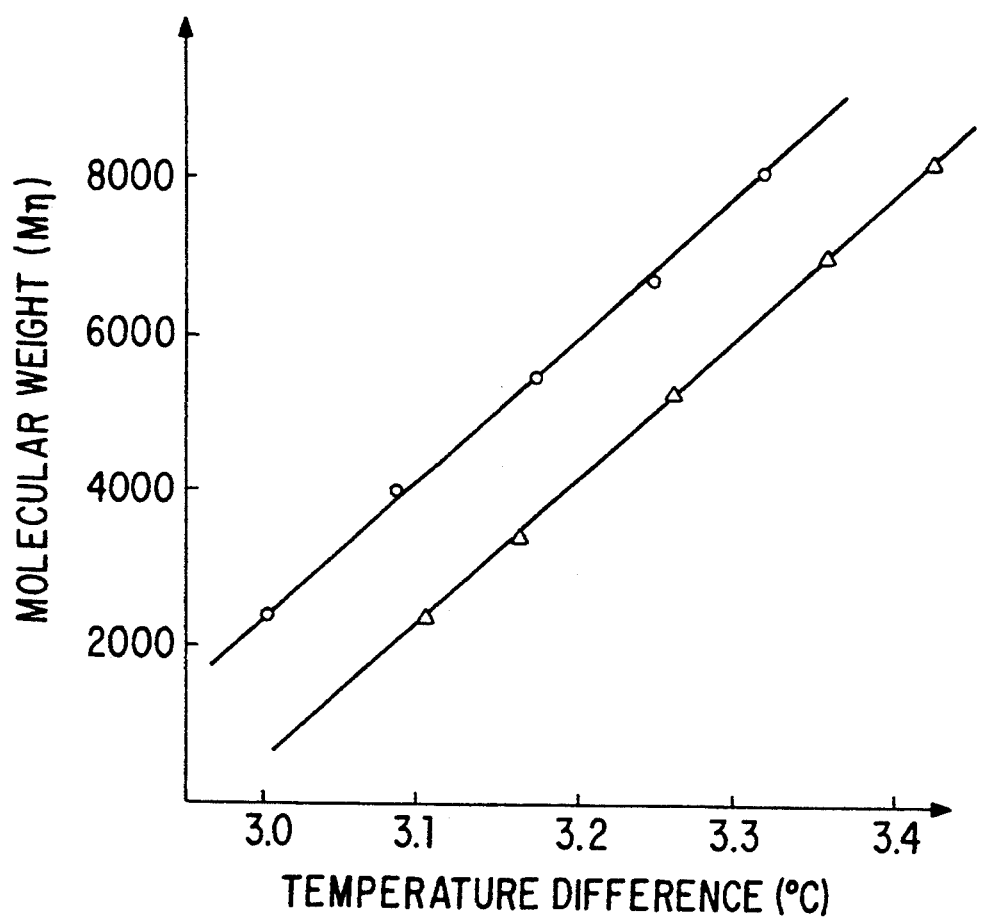
FIG. 3 shows a graph in which results obtained in Example 2 are plotted together with the results of Example 1.

The data obtained in Example 2 together with the data obtained in Example 1 are shown in the graph of FIG. 3. In the graph, o indicates a datum in Example 1, and Δ indicates a datum in Example 2. In Example 2, the relationship between the temperature difference and the polymer molecular weight did not fit the calibration curve obtained in Example 1 but deviated a little from the calibration curve of Example 1 as seen from FIG. 2. However, it was found that the results of Example 2 were well fitted on a curve formed by moving the calibration curve obtained in Example 1 in parallel.

Therefore, it is not necessary to newly obtain a calibration curve when the kind of the polymer is unchanged. Provided that with respect to a given polymer, a relationship between the temperature difference and the molecular weight previously has been obtained as a calibration curve, a specific calibration curve for another polymerization operation can be obtained by merely measuring the molecular weight and the temperature difference at one point in time during the polymerization and shifting the previously obtained calibration curve accordingly so that it passes through the point defined by the molecular weight and the temperature difference during the new polymerization process.

Since the polymer molecular weight measurement can be carried out in real time according to the present invention, any decision regarding the next operation during the Polymerization process can be easily made so that the productivity of the polymerization process is improved.

What is claimed is:

1. A method for the measurement of a molecular weight of a polymer during a present polymerization thereof which comprises the steps of:

heating a polymer portion with heating means, measuring, with temperature measuring means, a difference between temperatures of at least two points of the polymer portion thereby determining an empirical point, each of said points being thermally influenced by said heating means differently from the other of said points, and establishing the molecular weight of the polymer which corresponds to the difference between the temperatures obtained by the measuring step according to a predetermined relationship between the temperature difference and the molecular weight of the polymer, wherein the predetermined relationship is obtained by first obtaining a calibration curve between the temperature difference and the molecular weight of the polymer in an earlier polymerization process, and then moving the calibration curve in parallel, while maintaining the shape of the calibration curve, so that the curve contains said empirically determined point measured during the present polymerization.

2. The method according to claim 1 wherein the heating means also works as the temperature measuring means which measures the temperature at one point of the at least two points.

* * * * *